(12) United States Patent
Walte et al.

(10) Patent No.: US 9,020,764 B2
(45) Date of Patent: Apr. 28, 2015

(54) METHOD AND DEVICE FOR THE DETECTION AND IDENTIFICATION OF GASES IN AIRPLANE INTERIOR SPACES

(75) Inventors: Andreas Walte, Schwerin (DE); Wolf Münchmeyer, Ehra-Lessien (DE); Mario Schmidt, Schwern (DE)

(73) Assignee: Airsense Analytics GmbH, Schwerin (DE)

( * ) Notice: Subject to any disclaimer, the term of this patent is extended or adjusted under 35 U.S.C. 154(b) by 462 days.

(21) Appl. No.: 12/921,487

(22) PCT Filed: Mar. 10, 2008

(86) PCT No.: PCT/DE2008/000422
§ 371 (c)(1),
(2), (4) Date: Sep. 8, 2010

(87) PCT Pub. No.: WO2009/112001
PCT Pub. Date: Sep. 17, 2009

(65) Prior Publication Data
US 2011/0015875 A1    Jan. 20, 2011

(51) Int. Cl.
*G01N 33/00* (2006.01)
*G01D 18/00* (2006.01)
(Continued)

(52) U.S. Cl.
CPC ...... *G01N 33/0032* (2013.01); *B64D 2045/005* (2013.01); *G01N 27/622* (2013.01)

(58) Field of Classification Search
CPC ............ G01N 1/2273; G01N 2015/0038; G01N 15/0618; G01N 1/2205; G01N 33/0047; G01N 1/26; G01N 1/2001; G01N 1/2285; G01N 27/622; G01N 33/0032; B64D 13/00

USPC ............ 702/22–24, 28, 32, 85, 189; 73/23.2; 250/281
See application file for complete search history.

(56) References Cited

U.S. PATENT DOCUMENTS

| 2,959,677 A | 11/1960 | Robinson et al. |
| 3,621,240 A | 11/1971 | Cohen et al. |

(Continued)

FOREIGN PATENT DOCUMENTS

| CN | 175 9312 A | 4/2006 |
| DE | 10235612 A1 | 2/2004 |

(Continued)

OTHER PUBLICATIONS

H. Muir, "Cabin Air Sampling Study Functionality Test", Cranfield University, online, Nov. 2007, S. 1-5, XP002504843.
(Continued)

*Primary Examiner* — Janet Suglo
*Assistant Examiner* — L. Anderson
(74) *Attorney, Agent, or Firm* — Norris McLaughlin & Marcus, P.A.

(57) ABSTRACT

The concept underlying the invention is the development of a generic method for the detection and identification of gases in airplane interior spaces and an associated device, which is small and manageable, has a simple design, and allows the immediate and simultaneous detection and identification of the gases to be examined. This is achieved in that the supply air of the airplane interior space (20) is fed to a measuring device (1) and the measurement results of the measuring device (1) are analyzed by means of mathematical methods. Such methods and the associated devices for the detection and identification of gases in airplane interior spaces are used in order to spot and verify gases, particularly odors and explosive gases and/or gases harmful to people's health.

22 Claims, 4 Drawing Sheets

Figure 1:
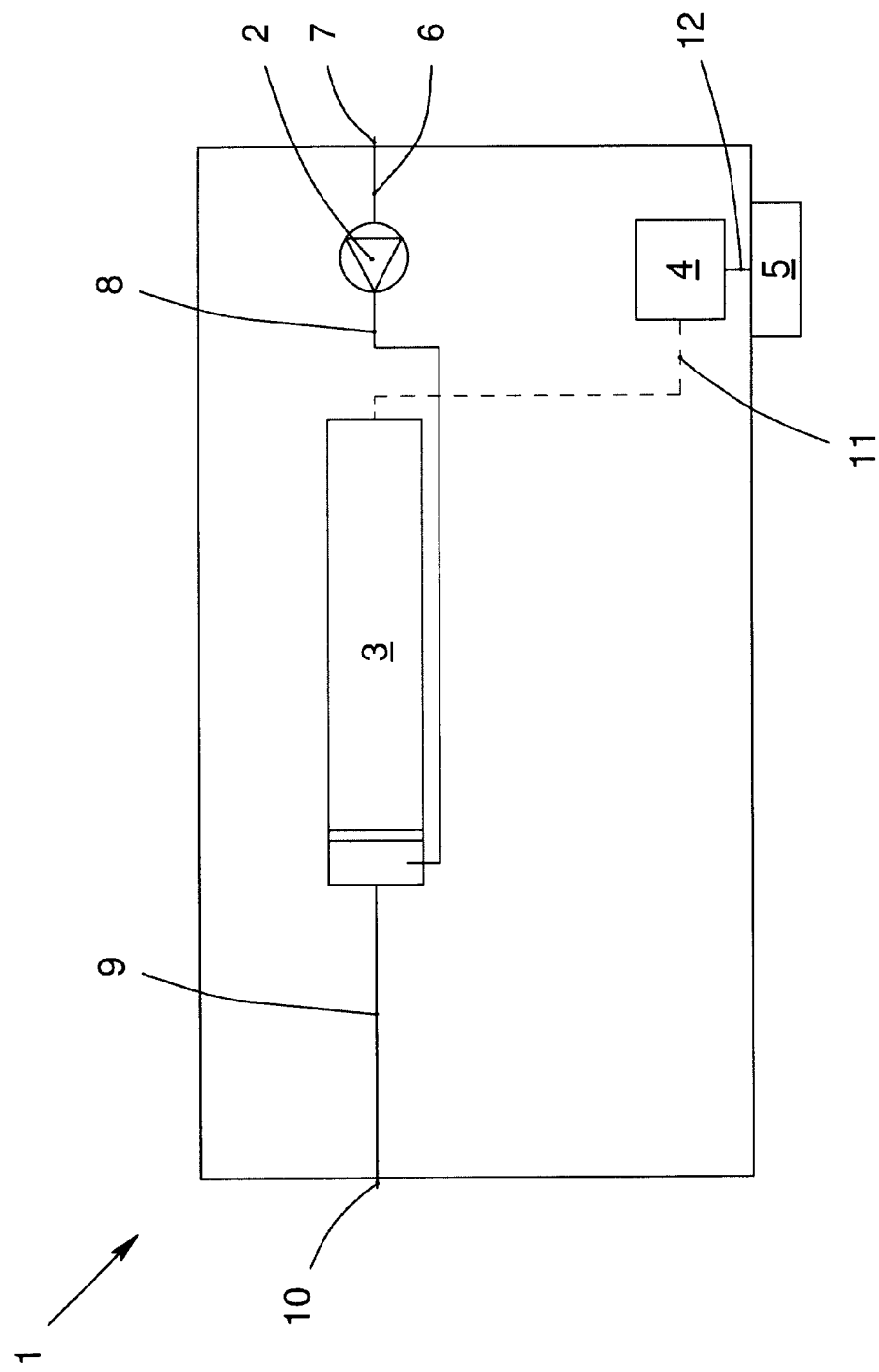

(51) Int. Cl.
   *G01J 3/00*    (2006.01)
   *G01N 27/62*   (2006.01)
   *H01J 49/04*   (2006.01)
   *B64D 45/00*   (2006.01)

(56) References Cited

U.S. PATENT DOCUMENTS

| | | | |
|---|---|---|---|
| 3,631,436 A | 12/1971 | Taguchi | |
| 3,925,183 A | 12/1975 | Oswin et al. | |
| 4,311,669 A | 1/1982 | Spangler | |
| 5,602,886 A * | 2/1997 | Gross et al. | 376/253 |
| 5,750,999 A * | 5/1998 | Fox | 250/343 |
| 2003/0071629 A1* | 4/2003 | Yang et al. | 324/464 |
| 2006/0115559 A1* | 6/2006 | Jones, Jr. | 426/231 |
| 2006/0219892 A1* | 10/2006 | Walte et al. | 250/288 |

FOREIGN PATENT DOCUMENTS

| | | |
|---|---|---|
| DE | 102 47 272 A1 | 4/2004 |
| JP | 2000-292403 | 10/2000 |
| JP | 06-082405 | 3/2006 |
| JP | 2006-519985 | 8/2006 |
| JP | 06-294772 | 10/2006 |

OTHER PUBLICATIONS

N.L. Nagda et al, "A Critical Review of Reported air Concentrations of Organic Compounds in Aircraft Cabins", Indoor Air, Bd. 13, 2003, S. 292-301, XP002504842 S. 292, 293.

Palmer P.T. et al, "Mass spectrometry in the U.S. Space Program: Past, Present, an Future", Journal of the American Society for Mass Spectrometry, Bd. 12, Nr. 6, Jun. 1, 2001, S. 656-675, XP004243274.

P.V. Johnson et al, "Ion Mobility Spectrometry in Space Exploration", International Journal of Mass Spectrometry, Bd. 262, Dec. 18, 2006, S. 1-15, XP002504844.

Mills, B., "Review of Methods of Odour Control", Filtration & Separation 2 (1995), p. 147-152.

G.A Eiceman and Z. Karpas "Ion Mobility Spectrometry" (2nd Edition, CRC, Boca Raton, 2005).

International Search Report dated Nov. 20, 2008.

Ampuero S et al: "The Electronic Nose Applied to Dairy Products: A Review", Sensors and Actuators B: Chemical: vol. 94, pp. 1-12, Aug. 15, 2003.

Gutierrez-Osuna, Ricard: "Pattern Analysis for Machine Olfaction: A Review", IEEE Sensors Journal, vol. 2, No. 3, Jun. 1, 2002.

Stanislaw Osowski: "Hybrid Neural Network for Gas Analysis Measuring System", pp. 440-445; Jan. 1, 1999.

Kolehmainen, Mikko, et al.; "Monitoring Odorous Sulfur Emissions Using Self-Organizing Maps for Handling Ion Mobility Spectrometry Data"; Journal of the Air and Waste Management Association; Jul. 2001; pp. 966-971; vol. 51; University of Kuopio, Finland; Kuopio, Finland.

Boger, Zvi, et al.; Use of Neural Networks for Quantitative Measurements in Ion Mobility Spectrometry (IMS); J. Chem. Inf. Comput. Sci.; May 1994; pp. 576-580; vol. 34, Nuclear Research Center, Beer-Sheva, Israel.

Daqi, Gao, et al.; "Simultaneous Estimationg of Odor Classes and Concentrations Using an Electronic Nose With Function Approximation Model Ensembles"; Sensors and Actuators B; Dec. 2006; pp. 584-594; vol. 120; University of Science and Technology, Shanghai, China.

McJunkin, Timothy R., et al.; "Toward an Intelligent Ion Mobility Spectrometer (IMS)"; International Journal for Ion Mobility Spectrometry; Jul. 2003; pp. 29-37; vol. 6; Idaho Engineering and Environmental Laboratory, Idaho Falls, Idaho.

* cited by examiner

METHOD AND DEVICE FOR THE DETECTION AND IDENTIFICATION OF GASES IN AIRPLANE INTERIOR SPACES

This application is a 371 application of PCT/DE2008/000422 filed on Mar. 10, 2008.

The invention relates to a method for the detection and identification of gases in airplane interior spaces and a corresponding device for using this method.

Such methods and the corresponding devices for detection and identification of gases in airplane interior spaces are used for identifying and detecting gases, in particular odors and explosive and/or harmful gases.

Odors are gases than can be detected by smell. Because impression from smell is subjective and different from one person to the other, an odor threshold value is introduced where more than 50% of the subjects detect the odorous substance. The concentrations of the odorous substance at the odor threshold value were determined and listed in table form for a number of odorous substances (e.g., in Mills, B.: Review of Methods of Odour Control, Filtration & Separation 2 (1995), p. 147-152).

The detection and identification of odors and explosive and/or harmful gases requires measurement methods with detection limits in the ppt to ppb range. Spectrometers are frequently used to detect and identify these gases. Preferred is the use of ion mobility spectrometers, which are also referred to as plasma chromatographs, because unlike other spectrometers, such as a mass spectrometer, they do not require a vacuum pump for generating a vacuum for the detection of gases. Ion mobility spectrometers therefore have a small installation size compared to other spectrometers and are very cost-effective. The field of application of ion mobility spectrometers is very large. It reaches from the medical field, for example testing the exhaled breath of patients, to application for production monitoring, for example in quality control in a coffee roasting plant and finally military applications, for example detection of chemical warfare agents. The general overview of ion mobility spectrometers and applications can be found, for example, in G. A Eiceman and Z. Karpas "Ion Mobility Spectrometry" (2nd Edition, CRC, Boca Raton, 2005).

Odors and explosive and/or harmful gases can also be detected in part using measurement systems which are composed of individual gas detectors or combinations of different gas detectors. The measurement signals of the individual gas detectors can then be compared with previously measured, as well as stored, signals, and the measured state can be described. For example, photo ionization detectors, electrochemical cells and metal oxide sensors can be used as detectors. Measurement devices supplying two-dimensional information, i.e., spectra, may also be used. Examples are mass spectrometers, Fourier transform infrared spectrometers, or ion mobility spectrometers.

Simple detectors, such as photo ionization detectors, electrochemical cells and metal oxide sensors with detection limits in the upper ppb and lower ppm range are too insensitive for detecting a number of gases. Moreover, their selectivity is frequently not sufficient to detect the harmful substances with the required reliability.

U.S. Pat. No. 2,959,677 discloses the essential functional features of a photo ionization detector. The gas to be detected is ionized with a UV lamp and subsequently electrically detected. Important is primarily the ionization potential of the compound to be detected. If the energy of the UV radiation is greater than the ionization energy of the compound, then the compound can be detected. Disadvantageously, many harmful substances cannot be detected. No spectral information is provided. It is also disadvantageous that the lamps of the photo ionization detector can be contaminated which results in poorer signal yields. U.S. Pat. No. 3,631,436 discloses essential functional features of the metal oxide sensors. These sensors react with reducing and oxidizing gases. They have a relatively strong cross sensitivity and cannot be used for detecting individual substances or as a warning indicator due to the high rate of false alarms. Metal oxide sensors have very short response times following gas exposure, but disadvantageously have significantly longer decay times. Electrochemical cells are more selective than metal oxide sensors. However, individual substances can still not be detected with those detectors, because cross sensitivity still exists and/or there are no electrochemical cells available for all substances. U.S. Pat. No. 3,925,183 discloses the essential functional features of the electrochemical cells.

The ion mobility spectrometer or the plasma chromatograph are known since some time. Unlike other spectrometers, they do not require movable or complex components in the ion mobility spectrometer, so that these systems can be designed to be small and inexpensive. A description of the individual components in an ion mobility spectrometer can be found, for example, in U.S. Pat. No. 3,621,240. The ion mobility spectrometer takes advantage of the different mobility of the ions. These devices have an inlet system, an ion source, whereby typically radioactive Ni63 foils are employed, an electrical drift tube which after a defined start separates the ions with an electrically switched grid depending on their mobility at atmospheric pressure, and a measurement sensor for detecting these small electric currents generated by the incident ions. Mainly air molecules are ionized in the ion source at atmospheric pressure, which subsequently ionize water clusters, also referred to as reactant ions. The harmful substances are subsequently ionized by proton transfer, electron transfer or proton abstraction reactions. By changing the polarity of the drift path, positive ions can be detected in the positive operating mode, whereas negative ions can be detected in the negative operating mode.

In mobile systems, the inlet is typically in the form of a membrane. U.S. Pat. No. 4,311,669 describes a membrane inlet system for ion mobility spectrometers.

Advantageously, the membrane reduces the effects of interfering quantities, such as humidity, pressure and temperature, on the measurement signal, so that the IMS system can be made small and portable. Disadvantageous, the membrane causes a somewhat more sluggish response time also measurement systems.

DE 102 35 612 A1 discloses a method and a corresponding device for monitoring the quality of lubricating oils, whereby a sample of the lubricating oil or the vapor emanating from the lubricating oil is withdrawn from a transmission; this sample is then supplied to an ion mobility spectrometer and the sample is analyzed with respect to the substances present in the vapor phase above the lubricating oil. Changes in the concentration and the type of substances in the sample are to be analyzed and evaluated through comparison with predetermined substances in the vapor phase of the unused lubricating oil to provide an actual state representative of aging of the lubricating oil. The ion mobility spectrometer is here connected to the transmission by way of a sample withdrawal line and also with an evaluation unit.

However, this solution has the disadvantage that the method and the corresponding device can only be used for monitoring the quality of lubricating oils in transmissions, because the device is only calibrated for lubricating oils of transmissions. A detection, meaning identification of the tested substance, if this is not lubricating oil of transmissions, it is therefore not possible. For this reason, this solution can also not be used in an aircraft interior space and/or for detecting gases of an aircraft, in particular for testing the maintenance state of aircraft engines.

Particularly disadvantageous with ion mobility spectrometers is also the very long time one has to wait until the system is ready to perform a measurement after the device has been turned on. The detector of the ion mobility spectrometer requires this time because it needs to flush from the system interfering substances that may have accumulated while being turned off. It is also disadvantageous that during short-term over-dosing systems are no longer measurement-ready and need to be flushed from several minutes to hours. It is also disadvantageous that the spectra are concentration-dependent. Another problem is the partially small selectivity of the ion mobility spectrometer. One reason is that, due to competing reactions in the ionization space, the harmful substances of interest are frequently not ionized and can therefore not be detected. These competing reactions may prevent many harmful substances with no proton affinity, for example many solvents, from being included in the spectrum if gases, such as ammoniac, are present.

Conversely, when solvents are present in higher concentrations (ppm), detection of components of interest can be made more difficult, if not impossible. The superimposed spectra in a gas mixture increase the frequency of false alarms.

In addition, harmful materials with lower proton affinity or electron affinity are not detected with the required detection limits.

Another disadvantage of the ion mobility spectrometer is the limited measurement range which spans, for example with a beta radiation source as an ionization source, typically maximally two orders of magnitude. This makes a quantitative conclusion difficult.

It is therefore an object of the invention to develop a generic method for detection and identification of gases in airplane interior spaces and a corresponding device, which is small and easy to handle, which has a simple construction and which allows immediate and simultaneous detection and identification of the gases to be tested.

This object is solved with a method and device having the characterizing features disclosed herein. Advantageous embodiments are also disclosed herein.

The novel method for detection and identification of gases in aircraft interior spaces and a corresponding device eliminate the aforementioned disadvantages of the state of the art.

Advantageously, when using the novel method for detection and identification of gases in aircraft interior spaces, the supply air of the aircraft interior space is conveyed to a measurement device and the measurement results of the measurement device are analyzed using mathematical methods. This makes possible an immediate and concurrent detection and identification of the gases to be tested. Advantageously, the mathematical methods may be divided into a calibration and a gas measurement, wherein the calibration includes dividing the measurement range of the measurement device into gas classes and an association of limit values for each gas class, and wherein the gas measurement includes identifying the gas classes and determining the gas intensity. The calibration is used for gases which are unknown to the measurement device, wherein the measurement device is trained on the unknown gases and a database is set up with a pair-wise arrangement of different measurement signals of the measurement device and limit values based on the limit value associated with each gas class. This method can then also be applied to unknown gases, because the unknown gases can be trained. In this way, the field of application can be readily expanded.

It is particularly advantageous when with odorous gases the calibration of the measurement device is performed for unknown odors, wherein the association of limit value for each gas class is set up in form of a database with pair-wise arrangement of different measurement signals of the measurement device and odor thresholds. The use of odor threshold values ensures that this method can be used in investigations of objectionable odors.

Advantageously, during a gas measurement a gas class may be selected while the gas classes for which the gas intensity is later determined are identified, wherein during the gas measurement the determined measurement results of the measurement device are compared with the previously recorded measurement results, with conclusions about the gas to be measured being drawn based on the comparison.

It is particularly advantageous if by changing the suction channel of the supply air of the aircraft interior space, or by changing the operating parameters in front of the suction channel, conclusions can be drawn regarding the gas sources of the gas to be measured in the suction region of the suction channel, wherein the conclusions are specific for the type of the gas source and the location of the gas source. By changes in the suction channel of the fresh air of the aircraft interior space, or changes of the operating parameter of an aircraft engine, for example, conclusions can be drawn regarding the maintenance state of an aircraft engine located in the suction area of the suction channel. In this way, the gas source can be easily and reliably localized. Because typically the largest portion of the air quantity for ventilating the aircraft interior space is operated in a closed loop, by deliberately closing off of the vent channels of the aircraft interior space, while simultaneously closing the fresh air supply and hence in the circulation operation of the ventilation, a gas or odor source can be localized in the aircraft interior space or eliminated. For example, in addition to odor sources, fires in the aircraft interior space, in particular cable fires underneath the interior trim of the aircraft interior space, can be localized. The remaining part of the air quantity of the ventilation of the aircraft interior space, which is not operated in closed loop, is fresh air which reaches the aircraft interior space by way of the aircraft engines, whereby conclusions can be drawn regarding the maintenance state of an aircraft engine located in the suction region of the suction channel by changing the suction channel of the fresh air of the aircraft interior space. If the intensity of the gas or odor of the gas to be measured has exceeded, for example, the odor threshold value or a limit value below or above the odor threshold value, and if the passengers in the aircraft interior space experience a significant unpleasant odor, then the suction channel of this aircraft engine and so localized aircraft engine are serviced during the next shutdown of the aircraft, allowing the corresponding leakage to be sealed.

It is furthermore advantageous if the subdivision of the measurement range of the measurement device into gas classes is performed with an artificial neural network, in particular a Kohonen-network and the association of-limit values for each gas class is accomplished with an artificial neural network, in particular a multilayer perceptron network. These artificial neuronal networks are particularly well suited for pattern recognition and hence have only a very low measurement uncertainty.

Advantageously, with the gas to be measured is drawn in with a feed pump and distributed by manifolds, and thereafter conveyed in parallel to an ion mobility spectrometer, an electrochemical cell, a photo ionization detector and/or two metal oxide sensors. The bandwidth of the identifiable gases and the range of applications are hereby further enhanced, so that the solution can also be applied to different gas mixtures. For example, different gases present in the tested a gas mixture can be simultaneously detected and identified.

It is particularly advantageous if the gas to be measured is mixed with a reference gas before reaching the ion mobility spectrometer, the electrochemical cell, the photo ionization detector and the metal oxide sensors, alternatively only before reaching the ion mobility spectrometer. The reference gas is hereby supplied in defined quantities to the gas to be measured, starting for example with the highest possible flow quantity of the reference gas, and then reduced. The measurement signal of the ion mobility spectrometer, the electrochemical cell, the photo ionization detector and/or the metal oxide sensors may be used for controlling the dosing of the reference gas, by directly using the relative signal amplitude of the metal oxide sensors, to briefly increase the gas flow of the feed pump, if the measurement signals of the metal oxide sensors should increase or in order to temporarily reduce the gas flow of the feed pump in the event that the measurement signal of the detector should decrease and/or to adjust from the measurement signal of the ion mobility spectrometer the absolute ranges of the gas flow quantity of the reference gas, if using the absolute signal values over a longer period of time to allow coarse adjustment, in particular for adjusting the maximum and minimum range of the conveyed quantity of the reference gas of the gas flow. This way, the detectors are handled gently, because poisoning of the detectors is prevented. On the other hand, this solution allows increasing the measurement range so that the breadth of the application can be further enhanced. The reference gas may consist of, for example, air filtered with activated charcoal, but may also include clean air with specific substances, so-called doping gases.

It is also advantageous if the gas to be measured is guided over a combination of the ion mobility spectrometer and the photo ionization detector for detection of aromatic substances, and additionally to the electrochemical cell for the detection of individual substances, such as phosgene, and additionally to the metal oxide sensors for the identification of, for example, hydrocarbons or carbon monoxide.

Advantageous with the application of the novel device for detection and identification of gases in aircraft interior spaces, a measurement device includes externally an intake fitting, a vent fitting and a control and display unit, wherein the measurement device and the ion mobility spectrometer and a feed pump may be located between the intake fitting and the vent fitting; an electronic computer may also be integrated. The suction side of the feed pump is connected with the intake fitting via a gas line, the ion mobility spectrometer and an additional gas line; the pressure side of the feed pump is connected to a vent fitting which is open to atmosphere. In addition, the computer is electrically connected via a line with the ion mobility spectrometer and likewise electrically connected via a line with the control and display unit. The device for detection and identification of gases in the aircraft interior spaces is small and easy to handle and has a simple structure. This is particularly advantageous, if the measurement device has in addition at least one photo ionization detector, at least one metal oxide sensor and/or at least one electrochemical cell, wherein each photo ionization detector, metal oxide sensor and/or each electrochemical cell are each arranged for fluid connection in parallel with the ion mobility spectrometer. The photo ionization detector can also be arranged, with reference to the flow, in series with the metal oxide sensor.

However, the photo ionization detector can also be arranged for fluid connection in series with the metal oxide sensor. This arrangement of detectors ensures a concurrent detection of the gases, so that the measurement time of this device is very short.

Advantageously, mathematical methods are integrated on the computer, wherein these mathematical methods are used for calibration and gas measurements. The calibration includes here a division of the measurement range of the measurement device into gas classes and an association of limit values for each gas class. The gas measurement, in turn, includes identification of the gas classes and determination of the gas intensity.

It is particularly advantageous if the measurement device is mobile or is fixedly installed in the supply air of the aircraft interior space. With a mobile measurement device, gas sources can be more easily localized in an aircraft interior space. However, the mobile measurement device allows use of the device outside an aircraft, e.g., for examining fluid accumulation underneath an aircraft or an aircraft engine.

Advantageously, the measurement device with the ion mobility spectrometer, the electrochemical cell, the photo ionization detector and/or of the two metal oxide sensors, which are connected via gas lines with a feed pump, wherein a system for controlled dosing of a reference gas by way of a feed pump are connected upstream of the ion mobility spectrometer, the electrochemical cell, the photo ionization detector and/or the two metal oxide sensors, and electronics with electronic computers and a control and display unit with an optical and acoustical alarm signal transducer.

The novel device for detection and identification of gases and the corresponding method for using the device will now be described with reference to three exemplary embodiments.

Figure 2:
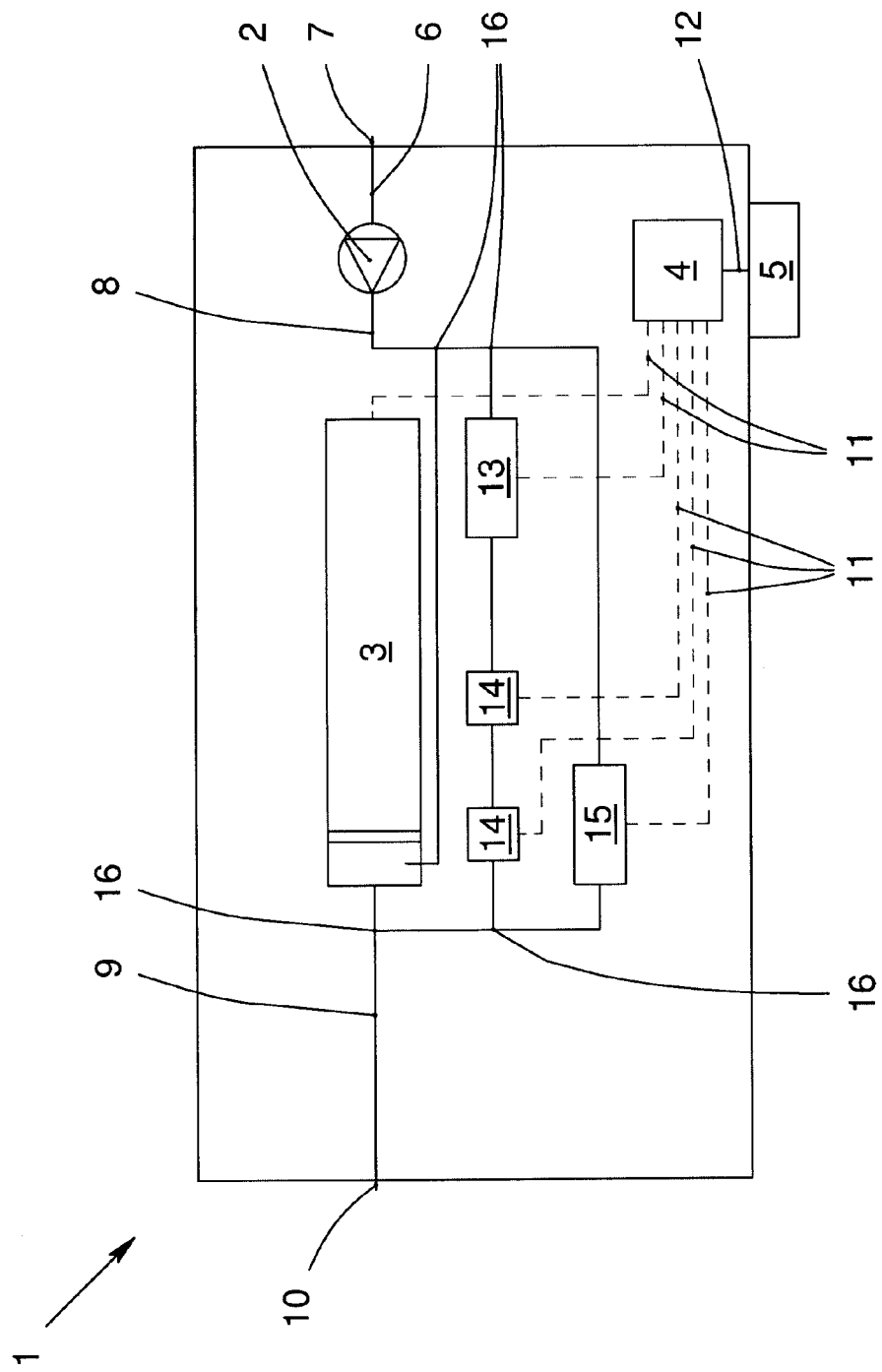
Figure 3:
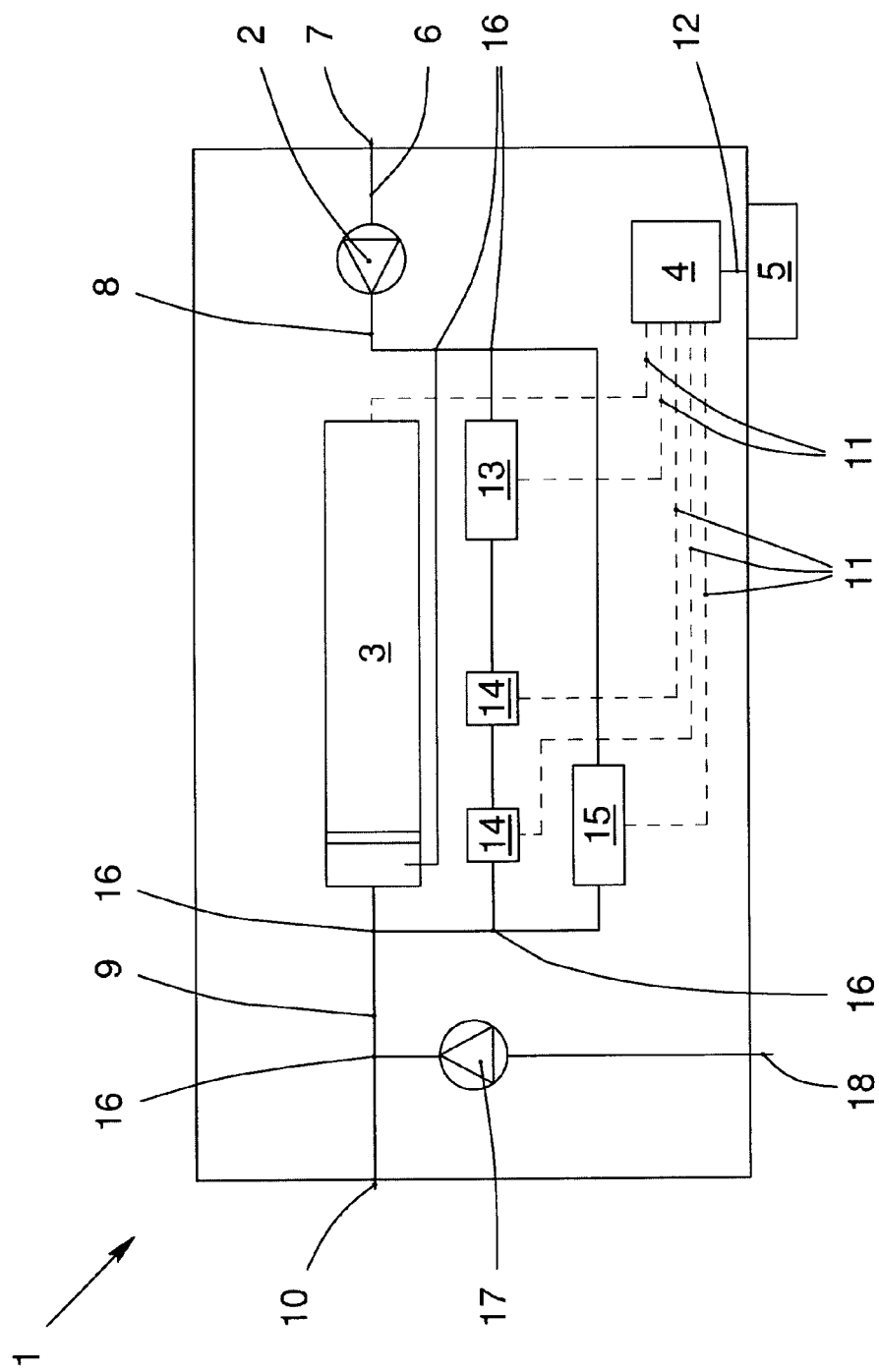
Figure 4:
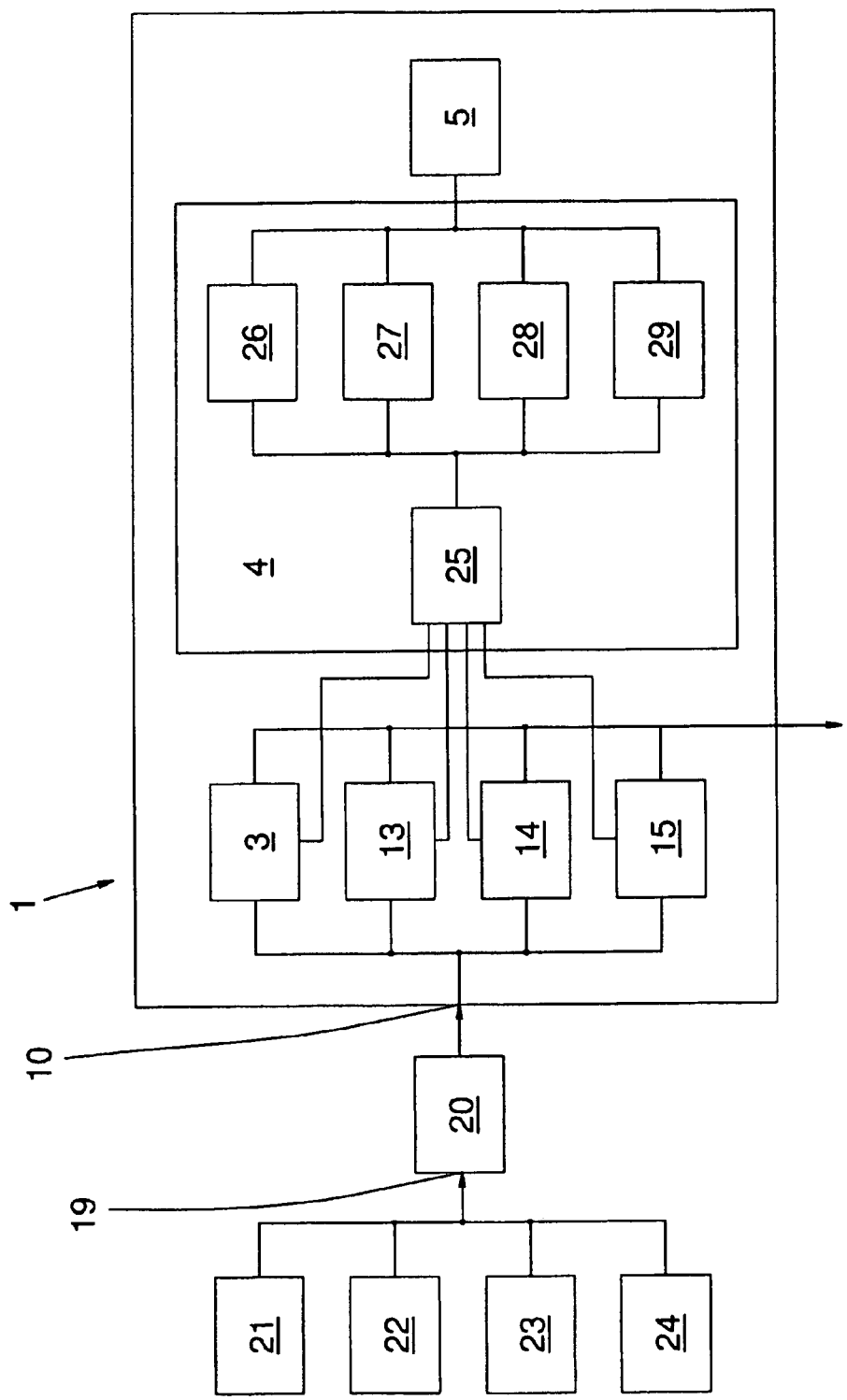

FIG. 1 shows a schematic diagram of the device in a first exemplary embodiment, FIG. 2 shows a schematic diagram of the device in a second exemplary embodiment, FIG. 3 shows a schematic diagram of the device in a third exemplary embodiment, and FIG. 4 shows a simplified diagram of the measurement arrangement and block diagram of the measurement of a gas in an aircraft interior space.

In a first exemplary embodiment according to FIG. 1. the novel device for identification of gases includes essentially a measurement device 1 with a feed pump 2, an ion mobility spectrometer 3 and an electronic computer 4 with a control and display unit 5.

The pressure side of the feed pump 2 is open to atmosphere by way of a gas line 6 with a vent fitting 7. Once the suction side, the output side of the feed pump 2 is connected via a gas line 8 with an of the ion mobility spectrometer 3, wherein the inlet side of the ion mobility spectrometer 3 is connected via a gas line 9 with an intake fitting 10.

In addition, the computer 4 is electrically connected via a line 11 with the ion mobility spectrometer 3 and via a line 12 with the control and display unit 5.

The control and display unit 5 provides a graphic and acoustic representation of the measurement results. In addition, the control and display unit 5 includes typical control elements, for example an ON/OFF switch or a START/STOP key for manual control of a measurement cycle.

In a second exemplary embodiment according to FIG. 2, the novel device for identification of gases has in addition a photo ionization detector 13, two metal oxide sensors 14 and an electrochemical cell 15.

The photo ionization detector 13 in conjunction with the metal oxide sensor 14 and the electrochemical cell 15 are each arranged in fluid communication in parallel with the ion mobility spectrometer 3. The flow channels 8 and 9 have each two manifolds 16. In addition, the photo ionization detector 13, the metal oxide sensors 14 and the electrochemical cell 15 are electrically connected with the computer 4 via an additional line 11.

It would also be feasible to use instead of the metal oxide sensor 14 a sensor array with identical and/or different metal oxide sensors 14.

In a third exemplary embodiment according to FIG. 3, the novel device for identification of gases has an additional feed pump 17 for controlled dosing of a reference gas, with the feed pump 17 extending via an additional manifold 16 located directly after the intake fitting 10 into the gas line 9, by which a reference gas can be supplied to the ion mobility spectrometer 3, the photo ionization detector 13, the metal oxide sensor 14 and the electrochemical cell 15 via the intake fitting 18.

It would also be feasible to use the feed pump 17 illustrated in FIG. 3 for controlled dosing of a reference gas only in combination with the ion mobility spectrometer, without additional sensors.

With all the aforementioned exemplary embodiments, computer programs using different mathematical methods are installed on the computer 4. These mathematical methods include a calibration and a gas measurement, wherein the calibration includes dividing the measurement region of the measurement device 1 into gas classes and associating limit values for each gas class; likewise, the gas measurement includes identification of the gas classes and determination of the gas intensity. The measurement region of the measurement device 1 is divided into gas classes and the limit values for each gas class are associated by a corresponding artificial neural network, wherein in particular a Kohonen-network for dividing the measurement region of the measurement device 1 into gas classes and a multilayer perceptron network can be used for the association of limit values for each gas class. However, in principle any other suitable artificial neural network or any other mathematical method for pattern recognition and for quantification can be employed.

In the division of the measurement region, the entire spectrum of the gases to be measured with the measurement device 1 is categorized in gas classes. The Kohonen-network is used for this purpose. This categorization is done in a training or learning phase. In the training or learning phase, the weighting functions of the individual neurons of the Kohonen-network are adapted to a training or learning data set. To this end, known gases are measured with a measurement device 1 and the obtained measurement signals are combined for each gas into data sets and stored. The gas classes are computed from the data sets for the Kohonen-network by a learning algorithm, wherein each gas class interprets a corresponding gas to be measured.

In the association of limit values for each gas class at least one limit value is associated with each gas class, wherein the multilayer perceptron network is used. These are limit values are, for example, gas concentrations producing objectionable and/or harmful odors. It would also be feasible that the limit value for gases or odors producing smell is the odor threshold.

The association of limit values to each gas class is again performed in a training or learning phase of the multilayer perceptron network, wherein this association is performed for each gas. To this end, predefined gas concentrations of the known gases to be measured are measured in the measurement device 1. The obtained measurement signals are combined for each gas concentration into data sets and stored. The association of limit values is computed from the data sets for each gas by a learning algorithm.

The learning algorithm for the division of the measurement region of the measurement device 1 into gas classes and the association of limit values for each gas class is the Gaussian least-square function, whereby however any other suitable method for minimizing the error can be used.

The operation of the novel device for identification of gases in aircraft interior spaces will now be described in an exemplary fashion with reference to the second exemplary embodiment. The measurement device 1, which according to FIG. 2 includes an ion mobility spectrometer 3, a photo ionization detector 13, two metal oxide sensors 14 and an electrochemical cell 15, is positioned with its intake fitting 10 in front of the supply air outlet 19 of the air supply in an aircraft interior space 20, so that only the air or the gas from the supply air outlet 19 reaches the intake fitting 10.

During the measurement process, the gas to be measured is suctioned in via the feed pump 2 and reaches via the intake fitting 10, the gas line 9 and the manifold 16 the ion mobility spectrometer 3, the electrochemical cell 15 and sequentially the photo ionization detector 13 and the metal oxide sensors 14. For fluid conduction, these individual gas flows are recombined via the manifolds 16 downstream of the ion mobility spectrometer 3, the electrochemical cell 15 and the photo ionization detector 13 and connected via the gas line 9 with the feed pump 2.

The electronic computer 4 separately processes the measurement data of the ion mobility spectrometer 3, the electrochemical cell 15, the photo ionization detector 13 and the metal oxide sensors and represents the results graphically or acoustically on the control and display unit 5.

For example, the ion mobility spectrometer 3 may only use the integrated measurement signals before and after the reactant ion peak. Because the system can operate in both negative and positive operating mode, four measurement channels are produced. In conjunction with the signals of the electrochemical cell 15, the photo ionization detector 13 and the metal oxide sensors 14 eight measurement channels are available in the aforedescribed configuration. If necessary, the spectrum of the ion mobility spectrometer 3 can also be more finely divided, so that significantly more than four channels can be used for the evaluation.

The channels can be used as input signals for subsequent pattern recognition. Feasible would also be an evaluation of the ion mobility spectrum such that only the resulting spectral peaks are taken into consideration in the subsequent evaluation.

Simple distance classifiers, for example a Euclidean distance classifier, discriminant classifiers or neural networks can be employed.

The ion mobility spectrum, i.e., the measurement signal of the ion mobility spectrometer 3, can also be displayed as a function of time.

According to the third exemplary embodiment illustrated in FIG. 3, the measurement device 1 may include an additional feed pump 17 for adding a reference gas into the gas line 9, wherein the admixed reference gas is also suctioned in by the aforementioned feed pump 2. In order to prevent damage to the ion mobility spectrometer 3, the electrochemical cell 15, the photo ionization detector 13 and the metal oxide sensors 14, the measurement device 1 is operated so that predominantly the reference gas is measured. With small measurement signals, the pump volume of the feed pump 17 is reduced, so that the fraction of the gas to be measured is increased. Addition of the reference gas may be performed in defined stages or may be controlled by the measurement signal from a detector.

It would also be feasible to alternatively intermix the gas to be measured with a reference gas only before reaching the ion mobility spectrometer 3 and to supply the gas to be measured to the other detectors, meaning the electrochemical cell 15, the photo ionization detector 13, and the metal oxide sensors 14, in a state undiluted by the reference gas.

It would also be feasible to store the measurement device 1 in a special preparation station when not in use. A feed pump in the preparation station ensures that the measurement device 1 is continuously purged with the reference gas, thereby preventing accumulation of mutually interfering components in the measurement device 1. Moreover, the measurement device 1 is ready for operation within several minutes. The preparation station can simultaneously also be used for charging batteries or reading measurement data stored in the measurement device 1.

When using the novel device for identification of gases in aircraft interior spaces, conclusions can be drawn about gas sources of the gas to be measured in the suction region of the suction channel by changing the supply air of the aircraft interior space. In particular, the type of the gas source and the location of the gas source can be determined.

In a stationary installation of the measurement device 1 according to FIG. 4 in the supply air outlet 19 of the ventilation of the aircraft interior space 20, the following process is performed in the event of gas or odor nuisance.

This supply air into the aircraft interior space 20 is suctioned in with the intake fitting 10 of the measurement device 1, wherein the supply air should have a fraction of fresh air which enters into the supply air in equal portions via the aircraft engines 21, 22, 23, 24.

If a gas or odor nuisance occurs, the gas class is first identified in the computer 4 with the calibrated measurement device 1 during gas measurement. The gas to be measured is then classified into a gas class. Exemplary gas gases may be:
- engine oils and lubricants (gas class A),
- kerosene (gas class B),
- exhaust gases of the aircraft engine (gas class C),
- burnt smell, i.e., maybe: monoxide, carbon dioxide and compounds of the incomplete combustion (gas class D).

A determination of the gas or odor intensity calibrated for this gas class is stored for each of these respective gas classes. It will be understood that, for example, the engine oils and lubricants themselves may be subdivided into several gas classes. Accordingly, four different evaluations are obtained for the aforementioned exemplary gas classes. Each gas class requires a determination of its own gas or odor intensity, meaning:
- determination of the gas or odor intensity 26 for the gas class A,
- determination of the gas or odor intensity 27 for the gas class B,
- determination of the gas or odor intensity 28 for the gas class C, and
- determination of the gas or odor intensity 29 for the gas class D.

For example, if the gas to be measured is classified in the gas class A, engine oils and lubricants, then first the origin of the gas to be measured can be localized by using the aircraft engines, so that one or several of the aircraft engines 21, 22, 23, 24 may have to be considered. When the odor threshold for engine oils and lubricants is exceeded, a severe odor nuisance may be experienced by the passengers.

Because the cabin cannot be adequately ventilated due to its size and hence the odor intensity cannot be eliminated, it is impossible to anticipate or conclusively determine a single specific engine as cause for the odor nuisance. The determination or exclusion of the aircraft engines 21, 22, 23, 24 is performed subsequently, wherein the results for the determination of the gas classes and odor intensity are immediately displayed on the control and display unit 5.

To this end, either the aircraft engines 21 and 24 or the aircraft engines 22 and 23 are brought to the same RPM. For example, if the aircraft engines 21 and 24 are brought to the same RPM, supply air is added to the aircraft engine 21 and supply air to the aircraft engine 24 is closed off. By measuring the supply air of the aircraft engine 21 with the measurement device 1, it can be checked if gas classes and odor intensities can be identified in the supply air. To this end, the measurement signals are initially evaluated by identifying the gas classes 25. If, for example, a gas class A for "engine oils and lubricants" is identified, then subsequently the gas or odor intensity 26 is determined for the gas class A. Thereafter, supply air is added to the aircraft engine 24 and the supply air to the aircraft engine 21 is closed off. At this point, the odor class may already have been detected first by the human sensory organ, although an association of the odor intensity is not possible. After the first detection of the odor intensity by the human nose, this odor impression remains, making an additional detection of the same odor class and odor intensity impossible.

The supply air of the aircraft engine 24 is now measured by the measurement device 1 with the goal to also determine the odor class and optionally the odor intensity.

The same process is then repeated with the aircraft engines 22 and 23. After this method has been terminated, the evaluation of the results of the measurement device 1 will allow to conclusively determine the supply air in which gas classes could be determined and their associated odor intensity.

It would also be feasible to attain increased odor intensity, instead of by adding the supply air to individual engines or by closing off the supply air from individual engines, by bringing the individual engines from an idling state to a higher RPM, thereby increasing the concentrations of the odorous compounds. Defective engines have significantly higher concentration awfully odorous compounds, for example lubricant and hydraulic oils.

The odor intensities are frequently below the odor threshold detectable by humans, so that a subjective impression would not have the desired success. The increase or decrease of the odor intensities can be detected and determined by adding the supply air via the aircraft engines 21, 22, 23, 24 and by continuously measuring the supply air with the measuring device 1.

In the evaluation of the gas classes and odor intensities from the results obtained with the measuring device 1, odor intensities are frequently determined which do not necessarily cause spurious odors in the aircraft interior space 20 and/or which are not yet detectable by the human nose. These gas or odor intensities can still allow conclusions about the state of the engine, so that it can already be determined if odor classes or odor intensities may be anticipated for certain aircraft engines in the future, before odor intensities are produced and detected by the passengers.

With a stationary installation of the measurement device 1 in the supply air outlet 19 of the ventilation of the aircraft interior space 20, it would also be feasible to electrically connect the computer 4 and/or the control and display unit 5 with an external control and display unit, which may be installed, for example, in the cockpit of the aircraft.

With a mobile measurement device 1, the location of the gas or odor source can be further limited by changing the measurement location.

For example, cable fires underneath the trim of the aircraft interior space may be localized by changing the measurement location across the trim of the aircraft interior space.

A mobile measurement device 1 is also capable to test unknown liquids, for example in form of a puddle, not only inside the aircraft interior space, but also outside the aircraft, for example underneath the aircraft engines.

It would also be feasible to use the measurement device 1 as a standalone unit or additionally with a Differential Mobility Spectrometer (DMS) or Field Asymmetric Ion Mobility Spectrometer (FAIMS spectrometer) or other suitably detectors for detecting the tested gases.

LIST OF REFERENCE SYMBOLS

1 Measurement device
2 Feed pump
3 Ion mobility spectrometer
4 Computer
5 Control and display unit
6 Gas line
7 Outlet air fitting
8 Gas line
9 Gas line
10 Intake fitting
11 Line
12 Line
13 Photo ionization detector
14 Metal oxide sensor
15 Electrochemical cell
16 Manifold
17 Feed pump
18 Intake fitting
19 Supply air outlet
20 Aircraft interior space
21 Aircraft engine I
22 Aircraft engine II
23 Aircraft engine III
24 Aircraft engine IV
25 Identification of the gas class
26 Determination of the gas or odor intensity for the gas class A
27 Determination of the gas or odor intensity for the gas class B
28 Determination of the gas or odor intensity for the gas class C
29 Determination of the gas or odor intensity for the gas class D

The invention claimed is:

1. Method for detection and identification of gases in aircraft interior spaces, wherein a supply air of an aircraft interior space of an aircraft is supplied to a measurement device comprising an ion mobility spectrometer, wherein measurement results of the measurement device are analyzed using mathematical methods, and the mathematical methods are divided into a calibration and a gas measurement, wherein the
calibration includes a partition of a measurement range of the measurement device into gas classes and in an association of limit values for each gas class, and
the gas measurement includes identification of the gas classes and determination of a gas intensity,
conclusions are drawn with respect to a maintenance state of an aircraft engine located in an intake region of an intake channel of the measurement device by (i) changing the intake channel of fresh air of the aircraft interior space, or (ii) changing at least one operating parameter of the aircraft engine, and
supply air comprises a fraction of fresh air entering into the supply air via a plurality of aircraft engines, wherein the intake channel of fresh air is changed by closing the supply air from an individual aircraft engine of the plurality of aircraft engines.

2. Method according to claim 1, wherein the calibration for the measurement device uses unknown gases, wherein the measurement device is being trained on the unknown gases and the association of limit values for each gas class is set up as a database with a pair-wise arrangement of different measurement signals of the measurement device and limit values.

3. Method according to claim 2, wherein, during the gas measurement, a gas class, for which subsequently the gas intensity is determined, is selected during identification of the gas classes, wherein, during the gas measurement, the determined measurement results of the measurement device are compared with previously recorded measurement results and conclusions are drawn from the comparison regarding the measured gas.

4. Method according to claim 3, wherein by changing the intake channel of the supply air of the aircraft interior space, or by changing operating parameters in front of the intake channel, conclusions are drawn with respect to gas sources of the measured gas in the intake region of the intake channel, wherein the conclusions relate to the type of the gas source and the location of the gas source.

5. Method according to claim 1, wherein for gases having an odor, the calibration of the measurement device is performed for unknown odors, wherein the association of limit values for each gas class is performed by setting up a database with pair-wise arrangement of different measurement signals of the measurement device and the odor threshold values.

6. Method according to claim 1, wherein
the partition of the measurement range of the measurement device into gas classes is performed with an artificial neural network, and
the association of limit values for each gas class is performed with an artificial neural network.

7. Method according to claim 1, wherein the gas to be measured is suctioned in by a feed pump and divided through manifolds, and is subsequently supplied in parallel to the ion mobility spectrometer, an electrochemical cell, a photo ionization detector and/or two metal oxide sensors.

8. Method according to claim 7, wherein the gas to be measured is intermixed with a reference gas before reaching the ion mobility spectrometer, the electrochemical cell, the photo ionization detector, and the metal oxide sensors, alternatively also before reaching the ion mobility spectrometer, by adding the reference gas to the gas to be measured in defined quantities, starting with the highest possible flow of the reference gas which is later reduced.

9. Method according to claim 8, wherein measurement signal from the ion mobility spectrometer, the electrochemical cell, the photo ionization detector and/or the metal oxide sensors is used for controlling dosing of the reference gas, by:
directly using relative signal height from the metal oxide sensors to briefly increase the gas flow of the feed pump, if the measurement signals from the metal oxide sensors are to increase, or to briefly decrease the gas flow of the feed pump if the measurement signal of the detector is to decrease, and/or
adjusting based on the measurement signal of the ion mobility spectrometer the absolute ranges of the gas flow amount of the reference gas by using the absolute signal magnitudes over a longer period of time to allow a coarse adjustment of the maximum and minimum range of the feed quantity of the reference gas in the gas flow.

10. Method according to claim 9, wherein the gas to be measured is conducted across a combination of the ion mobility spectrometer and the photo ionization detector for the detection of aromatic compounds, and additionally across the electrochemical cell for the detection of individual substances, and additionally across the metal oxide sensors for the detection of hydrocarbons or carbon monoxide.

11. Method according to claim 1, further comprising:
installing the device in the aircraft interior space.

12. Method according to claim 11, wherein the device is installed, mobile or stationary, in the supply air of the aircraft interior space.

13. Method according to claim 11, further comprising:
changing a measurement location of the device in the aircraft interior space.

14. Method according to claim 1, wherein the device is a mobile measurement device configured to test liquids inside the aircraft interior space or outside the aircraft.

15. Device for detection and identification of gases in aircraft interior spaces, with a measurement device comprising an ion mobility spectrometer, the measurement device further comprising an intake fitting, an outlet air fitting and a control and display unit, wherein the ion mobility spectrometer and a feed pump are arranged in the measurement device between the intake fitting and the outlet air fitting,
a suction side of the feed pump is connected with the intake fitting via a gas line, the ion mobility spectrometer and a gas line, and a pressure side is connected via a gas line to an outlet air fitting that is open to atmosphere;
an electronic computer is electrically connected with the ion mobility spectrometer via a line and also electrically connected with the control and display unit via a line and mathematical methods are integrated on the computer, wherein these mathematical methods are used for calibration and a gas measurement, wherein the
calibration includes dividing the measurement region of the measurement device into gas classes and an association of limit values for each gas class, and
the gas measurement includes identification of the gas classes and determination of a gas intensity, wherein
the measurement device is sized to be installable in a supply air of an aircraft interior space such that conclusions are drawable with respect to a maintenance state of an aircraft engine locatable in an intake region of the measurement device, and
the supply air comprises a fraction of fresh air enterable into the supply air via a plurality of aircraft engines, wherein an intake channel of fresh air is changeable by closing the supply air from an individual aircraft engine of the plurality of aircraft engines.

16. Device according to claim 15, wherein the measurement device has additionally at least one photo ionization detector, at least one metal oxide sensor and/or at least one electrochemical cell, wherein each photo ionization detector, metal oxide sensor and/or each electrochemical cell is arranged in parallel with the ion mobility spectrometer for fluid communication.

17. Device according to claim 16, wherein the photo ionization detector is arranged for fluid communication in series with the metal oxide sensor.

18. Device according to claim 15, wherein the measurement device is installed movable or stationary in the supply air of the aircraft interior space.

19. Device according to claim 15, wherein the measurement device is connected with the ion mobility spectrometer, the electrochemical cell, the photo ionization detector and/or the two metal oxide sensors, which are connected via gas lines with a feed pump, wherein an arrangement for controlled dosing of a reference gas by a feed pump is connected upstream of the ion mobility spectrometer, the electrochemical cell, the photo ionization detector and/or the two metal oxide sensors, the device further comprising electronics with electronic computers and a control and display unit with an optical and acoustic alarm signal transducer.

20. Device according to claim 15, wherein the device is a mobile measurement device.

21. Device according to claim 15, wherein the computer and display unit are electrically connected to an external control and display unit installed in a cockpit of an aircraft.

22. Method for detection and identification of gases in aircraft interior spaces, wherein a supply air of an aircraft interior space of an aircraft is supplied to a measurement device comprising an ion mobility spectrometer, wherein measurement results of the measurement device are analyzed using mathematical methods, and the mathematical methods are divided into a calibration and a gas measurement, wherein
the calibration includes a partition of a measurement range of the measurement device into gas classes and in an association of limit values for each gas class,
the gas measurement includes identification of the gas classes and determination of a gas intensity,
the gas classes comprise at least one gas class selected from the group consisting of (i) engine oils and lubricants, (ii) kerosene, (iii) exhaust gases of an aircraft engine, and (iv) burnt smell comprising monoxide, carbon dioxide and compounds of an incomplete combustion, and
wherein the supply air comprises a fraction of fresh air entering into the supply air via a plurality of aircraft engines, wherein the intake channel of fresh air is changed by closing the supply air from an individual aircraft engine of the plurality of aircraft engines.

* * * * *

UNITED STATES PATENT AND TRADEMARK OFFICE
CERTIFICATE OF CORRECTION

Page 1 of 1

PATENT NO. : 9,020,764 B2
APPLICATION NO. : 12/921487
DATED : April 28, 2015
INVENTOR(S) : Andreas Walte et al.

It is certified that error appears in the above-identified patent and that said Letters Patent is hereby corrected as shown below:

ON THE TITLE PAGE

[75] Inventors: "Mario Schmidt, Schwern (DE)" should read

Mario Schmidt, Schwerin (DE)

Signed and Sealed this
Twenty-fourth Day of November, 2015

Michelle K. Lee
*Director of the United States Patent and Trademark Office*